United States Patent
Job et al.

(10) Patent No.: US 6,319,677 B1
(45) Date of Patent: *Nov. 20, 2001

(54) GLOBULIN PROTEIN 11S, USABLE AS A SEED IMPREGNATION MARKER DURING GERMINATION

(75) Inventors: Claudette Job; Dominique Job, both of Lyons; Alain Kersulec, Le Moustoir, all of (FR)

(73) Assignee: Aventis CropScience S.A., Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/510,631

(22) Filed: Feb. 22, 2000

Related U.S. Application Data (6362) Continuation of application No. 08/983,198, filed as application No. PCT/FR97/00815 on May 7, 1997, now Pat. No. 6,107,051.

(30) Foreign Application Priority Data

May 13, 1996 (FR) .................................................. 96 06184
Apr. 4, 1997 (FR) .................................................. 97 04370

(51) Int. Cl.⁷ .............................. C12N 15/29; C12Q 1/68; G01N 33/53
(52) U.S. Cl. ..................... 435/7.92; 47/57.6; 47/DIG. 9; 436/63; 436/86
(58) Field of Search .................................... 530/370, 372, 530/373, 374, 375, 376, 377, 378, 379; 47/57.6, 58.1, DIG. 9; 436/501, 63, 86, 87; 435/7.1, 7.92, 7.93, 7.94, 7.95, 410, 430, 430.1; 504/100, 189

(56) References Cited

U.S. PATENT DOCUMENTS 5,837,820 11/1998 DeRose et al. .................... 530/370

6,107,051 * 8/2000 Job et al. ........................... 435/7.92

FOREIGN PATENT DOCUMENTS

0658625A2 6/1995 (EP) .

OTHER PUBLICATIONS

Lambert et al. Application of High–Performance Liquid . . . J. Chromatography. vol. 402, pp. 159–172, 1987.*

Kruse et al., "Expression of heat shock proteins during development of barley", *Plant Molecular Biology*, 23 (1993) pp. 111–122.

Abernethy et al., "Thermotolerance is developmentally dependent in germinating wheat seed", *Plant Physiol.*, 89 (1989) pp. 569–576.

Coca et al., "Expression of sunflower low–molecularweight heat–shock proteins during embryogenesis and persistence after germination: localization and possible functional implications", *Plant Molecular Biology*, 25 (1994) pp. 479–492.

Culianez–Macia et al., "DIP: a member of the MIP family of membrane proteins that is expressed in mature seeds and dark–grown seedings of Antirrhinum Majus", *Plant J.*, 4 (1993) pp. 717–725.

Lambert et al., "Application of high–performance liquid chromatography to the assessment of subunit heterogeneity in plant 11S storage globulins", *Chemical Abstracts* (1987) 107:152972.

(List continued on next page.)

*Primary Examiner*—Jeffrey E. Russel
(74) *Attorney, Agent, or Firm*—BakerBotts LLP (57) ABSTRACT

The present invention relates to a protein which is induced in the course of the soaking of mature seeds of plants belonging to species of the families chenopodiaceae, compositae, labiatae and cucurbitraceae, and to its use as a molecular marker of a seed soaking process.

11 Claims, 8 Drawing Sheets

OTHER PUBLICATIONS

Ikuko et al., "Pumpkin (Cucurbita species) seed globulin II. Alterations during germination.", *Chemical Abstracts* (1976) 85: 1197385.s.

Hayashi et al., "Nucleotide sequence of cloned cDNA coding for pumpkin 11–S globulin β subunit", *Chemical Abstracts* (1988) 109: 143585z.

Lesnevich et al., "The storage globulins of sugarbeet seeds" (1988) Database CAB,DN 890729414.

Lesnevich et al., "Protein markers in identification of sugar beet varieties and lines" (1990) Database CAB, DN 911621141.

Borisyuk et al., "Electrophoresis study of Beta vulgaris proteins", *Chemical Abstracts* (1982) 96: 1190465.

Brinegar et al., "Isolation and characterization of chenopodin, the 11S seed storage protein of *quinoa* (*Chenopodium quinoa*)", *J. Agric. Food Chem.* (1993) 41: 182–185.

Dell'Aquila et al., "Regulation of protein synthesis in germinating wheat embryos under polyethylene glycol and salt stress", *Seed Science Research* (1992) 2: 75–80.

Ishibashi et al., "Stored mRNA in cotyledons of *Vigna unguiculata* seed: nucleotide sequence of cloned cDNA for a stored mRNA and induction of its synthesis by precocious germination", *Plant Molecular Biology*, 15 (1990) pp. 59–64.

Allen et al., "Developmental expression of sunflower 11S storage protein genes", *Plant Mol. Biol.* 5 (1985) pp. 165–173.

Hayashi et al., "Nucleotide sequence of cloned cDNA coding for pumpkin 11–S globulin β subunit", *Eur. J. Biochem.* 172 (1988) pp. 627–632.

Lawrence et al., "Mobilisation of storage reserves during germination and early seedling growth of sugar beet", *Physiologia Plantarum* 78 (1990) pp 421–429.

* cited by examiner

SEQUENCE LISTING

<160> NUMBER OF SEQ ID NOS: 2

<210> SEQ ID NO 1
<211> LENGTH: 14
<212> TYPE: PRT
<213> ORGANISM: beta vulgaris
<220> FEATURE:
<221> NAME/KEY: unsure
<222> LOCATION: 6
<223> OTHER INFORMATION:

<400> SEQUENCE: 1

Leu Glu Glu Thr Ile Xaa Ser Ala Lys Leu Thr Glu Asn Ile
1               5                   10

<210> SEQ ID NO 2
<211> LENGTH: 14
<212> TYPE: PRT
<213> ORGANISM: pea
<220> FEATURE:
<221> NAME/KEY: PEPTIDE
<222> LOCATION: (1)...(14)
<223> OTHER INFORMATION: subunit beta of globulin 11S

<400> SEQUENCE: 2

Leu Glu Glu Thr Ile Cys Ser Ala Lys Ile Arg Glu Asn Ile
1               5                   10

GLOBULIN PROTEIN 11S, USABLE AS A SEED IMPREGNATION MARKER DURING GERMINATION

This is a continuation of application Ser. No. 08/983,198, now U.S. Pat. No. 6,107,051, which is the national stage of PCT/FR97/00815 filed May 7, 1997.

BACKGROUND OF THE INVENTION

The present invention relates to a protein which is induced in the course of the soaking of mature seeds of plants belonging to species of the families Chenopodiaceae, Compositac, Labiatae and Cucurbitaceae, and to its use as a molecular marker of the soaking phase involved in the germination of these seeds and in the osmoconditioning and hydroconditioning processes of these seeds, called pre-germination.

Germination is a complex developmental process, for which only few exact molecular data are currently available. This developmental programme, in the course of which the cells of the embryo change from a state of dormancy to a state of intense metabolic activity, is set up essentially during the soaking phase. In the physiological sense, it stops when the plantlet which bursts forth ruptures the seed, coats (Bewley & Black, 1983).

The main techniques used for defining the germination ability of seeds make use of traditional germination tests, that is to say the germination percentage is measured for a given batch of seeds under defined conditions at different points in time after sowing (temperature, humidity, light, substrate). The criterion which is generally used for quantitatively determining germination is the rupturing of the seed coat by an organ of the plant which bursts forth. Most of the biochemical markers described to date are correlated with this phase. Thus, they are, strictly speaking, not markers of germination, but rather of the initial growth phases (Fincher, 1989). It must be noted that the initial soaking phase (that is to say, the uptake of water) is reversible up to a certain point. After a controlled hydration of the seeds, they may be dried while preserving their biological integrity and their germination capacity. From the point at which the plantlet appears, commitment to growth becomes irreversible. In fact, dehydration at this stage irreparably leads to the death of the plantlets (Bewley & Black, 1983).

The pre-germination methods which have been developed by seed companies are based on the reversibility of the initial soaking phase. In general, the seeds are hydrated in a controlled manner and then dried (Coolbear et al., 1987; Karsen et al., 1989; Tarquis & Bradford, 1992). These methods add real extra value to the seeds because they allow
1) batches of seeds to be homogenized in relation to germination,
2) an appreciable saving of time to be achieved for emergence after sowing, since a certain number of biochemical processes, which are required for accomplishing germination, will already have been taking place during the treatment,
3) an improvement of the germination quality of old batches of seeds, probably on account of the fact that the repair mechanisms of the biological structures which have been damaged during the final maturation of the seeds, namely during storage, are set up during the treatment.

The optimization of such processes currently rests solely on carrying out germination tests, which require several days of experimenting. Moreover, if the treatment fails (batches of seeds are by nature heterogeneous, it in therefore necessary to optimize the treatment for each batch), the batch is lost. The possibility of continuously monitoring the soaking phase by means of an easily detectable molecular marker would therefore represent considerable progress which would allow the pre-germination treatment to be adapted to each batch of seeds.

SUMMARY OF THE INVENTION

The present invention is based on revealing the solubilization of a protein of plant origin which is induced in the course of seed soaking, originates from a crop plant species, comprising at least one unit of 18 to 25 kDa, is expressed in the seeds and in any other plant organ and which appears in large amounts during pre-germination processes which make use of a controlled uptake of water by the seeds.

DETAILED DESCRIPTION OF THE INVENTION

More particularly, the present invention relates to an isolated pure protein, named SIP protein, which consists essentially of globulin 11S which originates from soaked seeds of Chenopodiaceae, for example beet, spinach and fat hen, but also in other families such as, for example, Compositae such as, for example, chicory and camomile, the Labiatae such as, for example, dead nettle, or else the Cucurbitaceae such as, for example, courgettes. In the case of beet, the protein is called SIP.

The invention also relates to novel polyclonal or monoclonal antibodies, called anti-SIP, characterized in that they recognize at least one epitope carried by the protein defined above.

It also relates to the use of the specificity of tissue expression and the development pattern of these markers to measure as precisely as possible the stage of progress of seed soaking, either in the course of germination, or in the course of seed pre-germination processes, in particular their use as molecular markers for soaking seeds of Chenopodiaceae, for example beet or spinach, but also in other families such as, for example, the Compositae such as, for example, chicory and camomile, the Labiatae such as, for example, dead nettle, or else the Cucurbitaceae such as, for example, courgette. The detection of these markers is carried out with specific anti-SIP antibodies.

This detection can be made with the help of a device (kit), which is also part of the invention.

Characterization of a Protein which is Induced by Soaking Seeds During Pre-germination Processes The material used is the seed of sugar beet (*Beta vulgaris*, cultivar Univers) and three known pre-germination methods as test models. The seeds used have previously not undergone any treatment, and their average hydration level is in the order of 12%. The pre-germination methods used are, on the one hand, hydroconditioning of seeds at low temperature in the presence of pure water (Coolbear et al., 1987), on the other hand osmoconditioning of seeds in the presence of an inert osmotic, namely polyethylene glycol (PEG) 6000 (Tarquis & Bradford, 1992) and, finally, prehydration of seeds (Hegarty, 1978).

1) Pre-germination Method by Hydroconditioning at Low Temperature

This method has been described in the case of tomato seeds (Coolbear et al., 1987). The principle of it is to soak the seeds under defined conditions, at a temperature which is sufficiently low to avoid germination of the seeds. After the treatment, the seeds are dried, which allows them to be stored. This method is adapted here to beet seeds. The germination experiments and pre-germination experiments are conducted as follows. Each experiment is based on a batch of one hundred beet seeds, which are placed into Petri dishes (12×12 cm) on 3 layers of filter paper soaked with 6 ml of distilled water. The seeds are covered with one sheet of filter paper which, acting as a wick, allows the seeds to be soaked on their entire surface, and the dishes are then closed with their cover in order to minimize evaporation of water. The dishes are then placed into control-temperature cabinets in the dark. The germination curves obtained for each temperature as shown by the development of the total germination rate (expressed in % of the total number of seeds tested) as a function of germination time are characterized by three phases. Firstly, a latent phase, during which no germination takes place and during which the seed hydrates. The duration of these latent phases increases with lower incubation temperature. For example, it is 32 hours at 25° C., 44 hours at 20° C., 65 hours at 150° C., 120 hours at 10° C. and 320 hours at 5° C. Secondly, a phase of increasing the germination rate, where the rate increases with the incubation temperature within the range tested from 5° C. to 25° C. This rate also characterizes the homogeneity of the batch of seeds tested. The more homogeneous the germination capacity of the seeds, the higher this rate, and vice versa. Thirdly, a plateau is reached which characterizes the maximum germination number of the batch of seeds in consideration. When beet seeds, incubated for 11 days at 5° C. under the above-described conditions and none have germinated, are removed and dried at 20° C. to a hydration level of 10%, these seeds germinate much more rapidly than the control seeds which have not undergone any pretreatment. For example, in the case of seeds which have been treated for 11 days at 5° C., the latent period of the germination curve at 15° C. is only 25 hours in comparison with a latent period of 65 hours in the case of control seeds. This procedure, as described by Coolbear et al. (1987) for tomatoes, thus allows efficient pre-germination of beet seeds. In the case of beet, it is advantageous to use low temperatures (for example 5° C.) since, while hydroconditioning is more rapid at 20 and 25° C., it is also more difficult to control; the seeds germinating easily at higher temperatures. At 5° C., on the other hand, any radicule emergency is blocked during the important periods, which extend over several days, while allowing the controlled hydration of the seeds. At low temperature, there is good uncoupling in the course of time between the soaking process and the germination process. Such an uncoupling process, and the fact that radicule emergence is severely blocked at 5° C., additionally allow better control of the subsequent dehydration of the primed seeds without the risk of deterioration of the batch of seeds (in fact, hydration is reversible up to the point where the seeds germinate). In this manner, this drying step permits storage of the treated seeds for several months.

In parallel with these germination studies, some of the seeds are removed at different times of incubation at controlled temperatures to carry out biochemical analyses. To this end, crude extracts of the total and soluble proteins are carried out in the following manner: the seeds are crushed in a Waring-type blender for 60 seconds in the presence of liquid nitrogen, the powder is taken up in a homogenization buffer (Hepes pH 8.0) which contains various protease inhibitors (benzamidine-HCl, phenylmethylsulphonyl fluoride, $\epsilon$-amino caproic acid), the mixture is centrifuged (for 30 minutes at 20,000 g in Eppendorf-type centrifugation tubes) to eliminate cell debris, assays based on traditional techniques of separating proteins from the extract are carried out on polyacrylamide gel in the presence of SDS. This latter technique has been optimized for allowing the use of microanalysis materials for the electrophoresis of proteins on preformed polyacrylamide gels (PhastSystem and Phast-Transfer by Pharmacia), which have the advantage of analysing samples very rapidly (electrophoresis and staining of the proteins in the gel with Coomassie Blue are carried out in less than one hour; 16 samples are analysed simultaneously) and with a small amount of material (1 µl of protein sample per track of the gel). This apparatus also carries out the electrophoretic transfer of the proteins in the gel onto a nitrocellulose sheet in accordance with the method of Towbin et al. (1979), which subsequently allows individual proteins of the test extract to be identified with specific antibodies ("Western Blot" method).

Using these methods, we have observed the strong induction of a protein of molecular weight (22±3) kDa during the hydroconditioning of beet seeds at 5° C. We call this protein SIP (for Seed Imbibition Protein). It exists at a base level in untreated control seeds and becomes very plentiful in treated seeds (5 to 7 times the base level of the controls) and accounts for approximately 5 to 10% of the soluble proteins in pre-germinated seeds.

The SIP protein was purified to homogeneity from a proteinic extract (prepared as described above) of beet seeds which had been pre-germinated by the hydroconditioning process at 5° C. (carried out as described above). The proteins of the extract are separated electrophoretically in a preparative polyacrylamide gel at 20% in the presence of SDS. After electrophoresis, the SIP protein, which has been localized on the basis of its weight and its migration, is electroeluted from the gel by the method of Teissere et al. (1990). The solution is then centrifuged (6000 g) on Filtron Green, which allows concentration of the sample and elimination of most of the SDS.

This sample was used for immunizing a rabbit (sequence of 3 injections of 100 µg SIP in the presence of Freund's complete adjuvant, the first one at time zero, and the next two at 3 weeks and 7 weeks after the first). The antibodies thus obtained (anti-SIP), which are also part of the invention, allow approximately 5 ng of SIP protein to be detected at a dilution of 1/6000 using traditional ELISA methods on multiwell plates.

2) Method of Pre-germination by Osmoconditioning

This pre-germination method has been described by several authors, for example by Tarquis & Bradford (1992) for lettuce seeds. It works on the principle of incubating the seeds in the presence of an inert osmotic, namely PEG, in order to inhibit germination, that is to say radicule emergence, while allowing hydration of the seeds. The seeds which have been treated in this way are then dried, which allows them to be stored. In the osmoconditioning of beet seeds, the same method is used as for the hydroconditioning, except that the seeds (one hundred seeds per box of dimensions 12×12 cm) are incubated at 20° C. in the presence of 6 ml of distilled water which contains polyethylene glycol (PEG 6000). By adjusting the concentration of PEG 6000, various osmotic potentials can be obtained (Michel & Kaufmann, 1973). Lowering the osmotic potential entails a progressive slow-down of the germination rate. Thus, at −7.5, −10, −15 and −20 bar, no radicule emergence can be observed over at least 200 hours at 20° C. The control seeds which have been incubated in the absence of PEG 6000 germinate after a latent phase of 50 hours. When the beet seeds which have been incubated for 8 days at 20° C. and at −7.5 bar under the above-described conditions, of which none has germinated, are removed, washed briefly to eliminate the PEG 6000 solution, and dried at 20° C. to a hydration level of 10%, these seeds germinate much more rapidly than the control seeds which have not undergone any pretreatment. For example, in the case of seeds which have been treated for 8 days at 20° C. and −7.5 bar, the latent time of the germination curve at 20° C. is less than 8 hours in comparison with a time of 50 hours in the control seeds. This treatment method, which has been described for example by Tarquis & Bradford (1992) for the pre-germination lettuce seeds, therefore also allows effective pre-germination of beet seeds.

Using these methods, we have observed a strong induction of SIP protein during the osmo-conditioning process (8 days soaking at 20° C. in the presence of PEG 6000 giving osmotic potentials of −7.5 bar, −10 bar and −15 bar).

3) Method of Pre-germination by Prehydration

The prehydration method used is based on protocols published for the pre-germination of lettuce seeds (Tarquis and Bradford, 1992) and for studying the accelerated ageing of onion seeds (Dearman et al., 1986). It works on the principle of varying the water content of sugar beet seeds as follows. Dry mature sugar beet seeds are introduced into a cylindrical plastic tube (h=7 cm, d=3 cm) which is closed by an air-tight screw top. A piece of absorbent paper soaked with a specific amount of water is also introduced into the tube. The tube which contains the seeds in contact with the soaked paper is then placed on a roller rack in an incubator whose temperature is set at 20° C. ±1° C. in the dark. After the incubation, the seeds are weighed to determine the increase in their water content, and they are then dried at ambient temperature (approximately 16 hours) to return the water content to a value in the order of 10% based on dry weight. This drying step allows the treated seeds to be stored. Under the standard conditions of pre-germination by the prehydration treatment, 2.5 g of seeds (based on fresh weight) and 0.82 g of absorbent paper soaked with 0.81 ml of water are used. The standard treatment lasts for 2 days at a temperature of 20° C. ±1° C., which allows the water content of the treated seeds to be brought to a value of 30% ±1% based on dry weight. Under these conditions, no seed germinates during incubation. The same holds true when incubation is carried out for 5 days. After 8 days of incubation, however, around 29% of the seeds have germinated.

Pre-washing the sugar beet seeds has proved necessary for an efficient treatment of the sugar beet seeds by the prehydration method. This washing is carried out under the following conditions. The dry mature sugar beet seeds (2.5 g based on fresh weight) are immersed into 50 ml of water, with careful agitation. Washing takes 4 hours at ambient temperature (around 20–21° C.). After washing, the water content of the seeds is around 55% based on dry weight. The washed seeds are then dried as above for 16 hours at ambient temperature, which brings their water content to a value of around 10%. The washed and then dried seeds are then subjected to the above-described prehydration treatment.

In this part of the study, three types of sugar beet seeds were used: mature dry untreated seeds (termed controls), seeds which had been washed and treated by prehydration (termed washed and pre-germinated) and seeds which had not been washed (that is to say control seeds), but subjected to prehydration treatment (termed unwashed but pre-germinated).

Using these methods, we have observed that the washed and pre-germinated sugar beet seeds (that is to say seeds which have been subjected to the complete pre-germination treatment including washing and prehydration treatment) germinated much more rapidly than the corresponding control seeds. In contrast, the unwashed, but pre-germinated seeds (that is to say seeds which had been subjected to an incomplete pre-germination treatment without pre-washing) germinate at a rate which is comparable with that of the control seeds. Thus, only the complete treatment (washing+ prehydration) brings about a physiological effect in which the germination rate of sugar beet seeds is increased, which is characteristic of pre-germinated seeds. It is possible that pre-washing eliminates germination inhibitors contained in the seed coats of the sugar beet (Snyder et al., 1965; Battle and Whittington, 1969; Khan et al., 1983; Morris et al., 1984).

The content in soluble SIP of different seed samples was analysed in parallel with these germination experiments.

It has been observed that the SIP protein (subunit β of globulin 11S) was present in much higher quantities (around 5 times) in the soluble-protein extracts of washed and pre-germinated seeds in comparison with the same extracts produced from control seeds. Thus, the method of pre-germination by prehydration leads to the same results as those obtained with the methods of hydroconditioning at 5° C. and osmoconditioning in the presence of PEG 6000. As for the soluble-protein extracts of unwashed but pre-germinated seeds, they only contain a low level of soluble SIP protein, which is equivalent to that of the control seeds. This result demonstrates that a positive correlation exists between successfully subjecting sugar beet seeds to pre-germination and the presence of copious quantities of SIP protein in the soluble-protein extracts.

Total-protein extracts from various seed samples have also been analysed. To this end, the above-described SDS extraction buffer (2% vol/vol) is added. In this case, it has been observed that the total-protein extracts from control seeds, both unwashed but pre-germinated and washed and pre-germinated, contained the same amount of total SIP (that is to say, SDS-extractable). The total amount of SIP which can be extracted by SDS-containing extraction buffer amounts to approximately 3 times the quantity measured in soluble-protein extracts of washed and pre-germinated seeds.

These studies were extended to 75 commercial sugar beet seed batches. In all these cases it was observed that the proteinic extracts of the washed and pre-germinated sugar beet seeds contained an amount of soluble SIP (that is to say extractable without SDS) which amounts to approximately 30–35% of the total SIP protein level (that is to say extractable in the presence of SDS). As for the soluble-protein extracts of the corresponding control seeds, they contained only a small amount of soluble SIP, less than 10% of the total SIP level. This allows an optimization of the use of the SIP marker as described in the paragraph "Procedure of a pre-germination process with the aid of a diagnostic kit" hereinbelow. Correlation between induction level of the SIP protein and priming intensity of the seeds The use of anti-SIP antibodies shows that the SIP protein is strongly induced (by a factor of 5 to 7) when subjecting the seeds to osmoconditioning in the presence of PEG 6000. The same is the case when carrying out hydroconditioning of the seeds in the presence of water alone at 5° C. In this latter case, the protein appears after an incubation time of 6.5 days under these conditions, the maximum level (approximately 6 to 7 times the base level of the untreated seeds) being reached after an incubation time of 11 days. The intensity of the pre-germination treatment of the seeds is characterized as follows. Seed samples are taken during the hydroconditioning treatment at 5° C., the samples are dried, and then they are again allowed to germinate at 15° C. For each of the samples the germination level obtained at a temperature of 15° C. for a fixed period of 63 hours is then determined. These data indicate that the longer the incubation time at 5° C., the higher the germination rate of 63 hours at 15° C. of treated seeds, that is to say the intensity of priming increases with the duration of hydroconditioning at 5° C. The use of anti-SIP antibodies shows that a positive correlation exists between the level of SIP synthesized during the treatment of the seeds and the intensity of the pre-germination treatment. These results demonstrate moreover the possibility of continuing the progress of a pre-germination process due to the use of anti-SIP antibodies and of a traditional ELISA technique. In the case of the sugar beet model (cultivar Univers), an increase by a factor of 6 to 7 of the SIP protein content of the treated seeds (relative to the base level of control seeds) corresponds to optimal pre-germination conditions for these seeds. When this SIP level is reached, the treatment must be stopped since a continuation would mean that there is the danger of some of the seeds germinating, and these unduly intensely treated seeds will be lost during the subsequent dehydration process, which is necessary for storing the treated seeds, thus resulting in a loss of quality of the batch of seeds treated (dehydration is not reversible after root emergence).

The kinetics of appearance and the quantitative determination of the SIP level while carrying out any pre-germination process of seeds are also part of the invention.
Characterization of Seed Proteins Induced During the Soaking Phase of the Germination The above results demonstrate a strong induction of the SIP protein when beet seeds undergo pre-germination processes. The question is to know whether the induction of this protein normally accompanies the germination process or if it takes place specifically as a response to the pre-germination processes used. To answer this question, germination experiments are carried out at the optimal germination temperature for beet seeds. Under defined germination conditions (one hundred seeds per Petri dish 12×12 cm, 6 ml of water per dish), such optimal germination is achieved in the range of 20° C. to 25° C. Measured under these conditions are, on the one hand, the total germination rate of the batches of beet seeds at different incubation temperatures in the incubator and, on the other hand, some of the seeds are removed at different times to quantitatively analyse the SIP level by carrying out crude extracts of the total and soluble proteins as described above using the anti-SIP antibodies. The protein exists at a base level in dry and mature seeds and it is then strongly induced during germination at a rate which is much higher than the radicules appear. Thus, the SIP level for seeds germinated at 20° C. is approximately three times as high, even though no seed has germinated yet. The amount of SIP protein then increases progressively up to its maximum value (5 to 7 times the base level), reaching its maximum value after 96 hours at 20° C., while the total germination percentage increases as well. Finally, the SIP protein disappears gradually after 96 hours' germination at this temperature, and growth of the plantlet takes place.

As a conclusion, the SIP protein is normally induced during soaking and germination of beet seeds.
Distribution of the Protein in the Tissue The use of the anti-SIP antibodies shows that expression of the SIP protein is seed-specific. It is not detected in vegetative organs of the plant such as leaves and roots.
Presence of Proteins which are Equivalent to the SIP Protein in Other Kinds of Seeds The possible presence of proteins which are equivalent to the SIP protein was investigated in various seeds. Having observed that, in the case of sugar beet (cultivar Univers), the SIP protein is induced during the early germination phases at 20° C., various batches of seeds were germinated (one hundred seeds per Petri dish, 6 ml of water per dish, T=20° C.). When the batches have reached 50% germination under these conditions, samples are taken. The use of anti-SIP antibodies shows that the protein is present in all germinated cultivars of seeds of sugar beet (Univers, Adonis, Alizé, Accord) and fodder beet (Monoval Géant Rouge, Eckendorf) which we have analysed, and in various Chenopodiaceae (spinach, fat hen), Papilionaceae (lupin, bean, pea, lucerne), Compositae (sunflower, chicory, camomile, lettuce), Labiatae (dead nettle), Cucurbitaceae (courgette, gherkin), Cruciferae (oilseed rape, mustard, radish, Arabidopsis thaliana) and Solanaceae (tomato). In the case of spinach, chicory, camomile, dead nettle and courgette, the level of proteins equivalent to the SIP protein increases greatly during germination. In these seeds, the antibodies identify one or more proteins (two in the case of chicory, three in the case of spinach and courgette) whose weight is around 204 kDa (18 to 25 kDa). It might therefore be the case that they are isoforms of the SIP protein (multigene family, or modifications after translation). In the case of species which belong to the family of the cereals (barley, maize, wheat, rice) and the family of the Umbelliferae (carrot), the reactivity of anti-SIP antibodies is very poor.

Identification of the SIP Protein

The SIP protein was identified as follows. The SIP protein was purified from a proteinic extract of sugar beet seeds which have been pre-germinated as described in the paragraph "Characterization of a protein which is induced by soaking seeds during pre-germination processes". Microsequencing from its N-terminal end, which was carried out by Edman degradation (Edman, 1956) with the aid of a 477A microsequencer from Applied Biosystems coupled to a 120A analyser from Applied Biosystems, gave the following amino acid sequence:

LEETIXSAKLTENI SEQ ID NO.1

This sequence is very close to the sequence found for the basic subunit (also named subunit β) of globulin 11S in many kinds of seeds. For example, the N-terminal sequence of the subunit β of globulin 11S of pea is

LEETICSAKIRENI SEQ ID NO.2

(Shewry et al., 1995).

A large number of studies were dedicated to these 11S globulins. They are proteinic complexes which belong to the family of the storage proteins of the seeds of dicotyledonous plants (Bewley and Black, 1994; Shewry et al., 1995; Müntz, 1996). Lawrence et al. (1990) have also shown that an 11S globulin exists in mature beet seeds and studied the degradation kinetics of this globulin during germination.

The 11S globulins are proteinic complexes formed by two subunits, one acidic subunit termed α and one basic subunit termed β. These two subunits are linked to each other in a covalent fashion by establishing a disulphide bridge between the chains. In the course of seed maturation on the mother plant, 11S globulins are stocked in specific cell organelles termed proteinic bodies (Bewley and Black, 1994). They are put together in these proteinic bodies in the form of hexamers which bring together six subunits α and six subunits β (Shewry et al., 1995). One of the physico-chemical characteristics of globulins is the fact that they are insoluble in water and in buffers of weak ionic strength. They can only be solubilized from mature dry seeds by extracting proteins in buffers which contain a denaturing agent (for example SDS, sodium dodecyl sulphate) or in buffers of high ionic strength (that is to say those which contain a higher concentration of salt; for example NaCl) (Bewley and Black, 1994; Shewry et al., 1995). The 11S globulins belong to the family of the seed storage proteins and they have the role of acting as a carbon and nitrogen source for the plantlet which bursts forth following germination of a seed (Bewley and Black, 1994; Müntz, 1996). They are mobilized (that is to say they undergo various proteolytic attacks by endoproteases and exoproteases) during seed germination, which allows them to be solubilized and fully degraded. These mobilization processes are generally considered as being post-germination events, that is to say they take place at, or after, radicule emergence.

Thus, the SIP protein is the subunit β of the 11S globulin of beet. It will be termed indiscriminately SIP protein or subunit β of the 11S globulin in the entire text of the present application.

This identification and the above results show that pre-germination of sugar beet seeds induces an early phenomenon (before germination) in the mobilization of the 11S globulin, which leads to the solubilization of its subunit β in an extraction buffer of weak ionic strength (Hepes buffer, used in the experiments mentioned in FIGS. 1A, 1B, 2, 3B, 4B, 4D, 5, 6 and 7).

Procedure of a Pre-germination Process with the Aid of a Diagnostic Kit

The present invention also relates to a process for the best procedure of a pre-germination treatment of seeds which, in the course of the treatment, produce a protein recognized by the anti-SIP antibodies of beet, such as seeds of the family of the Chenopodiaceae, for example beet, fat hen and spinach, but also in other families such as, for example, the Compositae such as, for example, chicory and camomile, the Labiatae such as, for example, dead nettle, or else the Cucurbitaceae such as, for example, courgette. The proposed diagnostic kit consists of these specific antibodies. It is complemented by secondary antibodies to rabbit antibodies (the anti-SIP being made in rabbits). These secondary antibodies are commercially available (for example Sigma for the antibodies to rabbit antibodies made in goats). They are coupled to peroxidase, which allows ready quantitative determination of the SIP protein (in the case of beet) or its equivalent (in the case of seeds other than beet) in proteinic extracts which leads to the extraction of all the soluble proteins as described for beet. This quantitative determination is carried out with a traditional ELISA method using multiwell plates and spectrophotometry for the development of the peroxidase reaction in the presence of peroxidase substrates [$H_2O_2$ and 2-2'-azinobis-(3-ethylbenzothiazoline-6-sulphonic acid), Aldrich] with the help of a multiwell plate reader (for example EL340 reader from Bio-Tek Instruments).

The procedure is as follows.

1) Preparation of soluble- and total-protein extracts from control seeds and seeds which have been treated in the course of pre-germination treatment.

2) Measurement of the soluble and total SIP level (subunit β of the 11S globulin) with the aid of anti-SIP antibodies and ELISA techniques described in the first patent.

3) Stopping the pre-germination treatment when the soluble SIP level (subunit β of the 11S globulin) reaches around 30–35% of the total SIP level.

The invention furthermore relates to a method of controlling the soaking, or water uptake, when the seeds germinate, be it naturally or in the course of the pre-germination treatment, characterized in that an SIP protein or an equivalent protein is used as molecular marker.

The examples which follow illustrate the isolation of the SIP protein, the role of the SIP protein and the equivalent proteins and their use for controlling the soaking, or water uptake, when seeds germinate, be it naturally or in the course of a pre-germination treatment.

EXAMPLE 1

Development of Total and SIP Proteins During the Pre-germination of Beet Seeds. Isolation of SIP Protein (A) Treatment of Beet Seeds by Hydroconditioning at 5° C.

Figure 1:
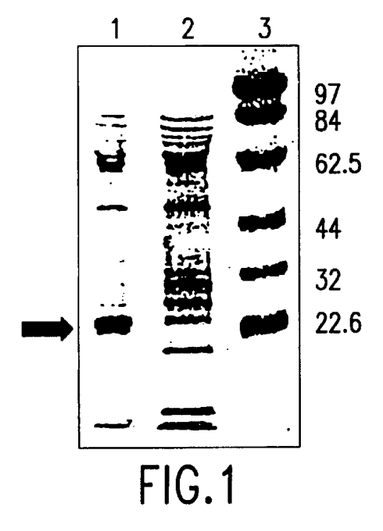
FIG. 1 is a polyacrylamide gel depicting the protein profile of hydroconditioned and untreated beet seeds.

The pre-germination experiments are conducted in accordance with the hydroconditioning process. The beet seeds are incubated for 11 days at 5° C. in the presence of 6 ml of water for one hundred seeds. The total and soluble proteins are extracted by grinding in a Hepes buffer (pH 8.0) which contains protease inhibitors. These proteins are analysed after polyacrylamide gel electrophoresis (20%), PhastSystem by Pharmacia, in the presence of SDS and staining of the proteins with Coomassie Blue. FIG. 1, track 1, shows the protein profile of treated seeds. Track 2 refers to untreated control seeds. Track 3 corresponds to the migration of standard proteins. Their molecular weight is indicated on the right-hand side of the photograph in kDa. The arrow indicates the migration of the SIP protein. It can be seen that it is strongly induced during the pre-germination process which the seeds undergo.

(B) Treatment of Beet Seeds by Osmoconditioning in the Presence of PEG 6000

Figure 2:
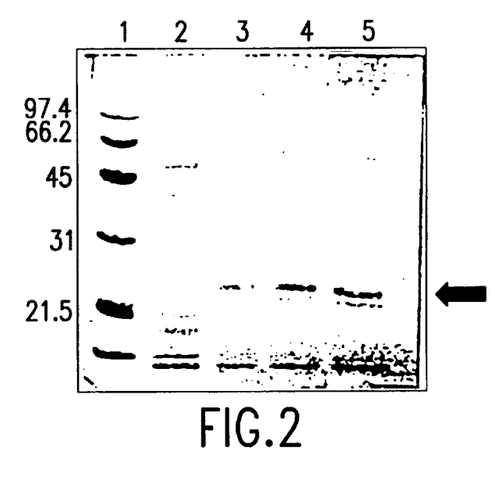
FIG. 2 is a polyacrylamide gel depicting the protein profile of beet seeds treated by osmoconditioning.

The pre-germination experiments are carried out in accordance with the osmoconditioning process. The beet seeds (one hundred seeds per batch) are incubated for 8 days at 20° C. in the presence of 6 ml of water containing PEG 6000, which gives osmotic potentials of −7.5, −10 and −15 bar. The total and soluble proteins are extracted by grinding the seeds as shown in FIG. 1. These proteins are analysed after polyacrylamide gel electrophoresis (20%), PhastSystem by Pharmacia, in the presence of SDS and staining the proteins with Coomassie Blue. FIG. 2, tracks 3, 4 and 5, show the protein profile of the seeds treated at −7.5, −10 and −15 bar. Track 2 refers to untreated control seeds. Track 1 corresponds to the migration of standard proteins. Their molecular weight is indicated on the right-hand side of the photograph in kDa. It can be seen that the SIP protein is strongly induced during the pre-germination process which the seeds undergo.

These two experiments show clearly the induction of the SIP protein in seeds which have been subjected to pre-germination processes of a very different nature.

(C) Purification of the SIP Protein After Treatment of Beet Seeds by Hydroconditioning at 5° C.

Figure 3:
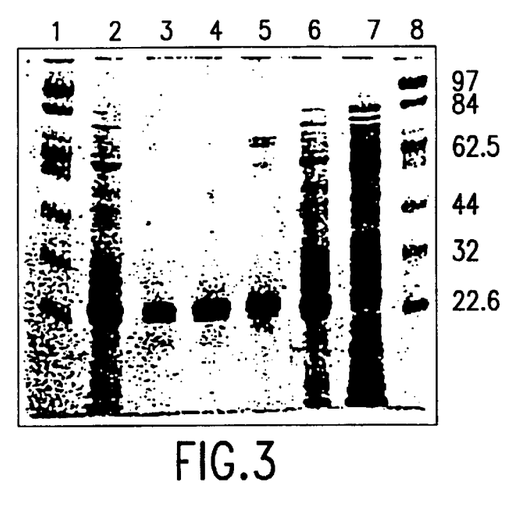
FIG. 3 is a polyacrylamide gel depicting the purity of different SIP preparations.

The pre-germination experiments are conducted in accordance with the hydroconditioning process as shown in FIG. 1. The total- and soluble-protein extract is prepared from seeds which have been treated at 5° C. for 11 days as shown in FIG. 1. This extract was deposited on a preparative polyacrylamide gel of 20% in the presence of SDS. After electrophoresis, a gel band corresponding to the SIP protein is excised, and the SIP protein is electroeluted from the gel. FIG. 3 (tracks 3, 4 and 5) shows the analysis of the purity of different SIP protein preparations by polyacrylamide gel electrophoresis (20%), PhastSystem by Pharmacia, in the presence of SDS and staining of the proteins with Coomassie Blue. Tracks 2 and 6 correspond to seeds which have been treated by hydroconditioning. Track 7 corresponds to untreated control seeds. Tracks 1 and 8 correspond to the migration of standard proteins. Their molecular weight is given on the right-hand side of the photograph in kDa.

EXAMPLE 2

Development of the SIP Protein in the Course of the Germination of Beet Seeds

The germination experiments are carried out in Petri dishes (12×12 cm) in the dark (one hundred seeds and 6 ml of water per dish) at a temperature of 20° C. On the one hand, the development of the total germination rate is measured as a function of time and, on the other hand, samples are taken to prepare crude extracts and quantitatively determine the SIP protein level as described.

Figure 4:
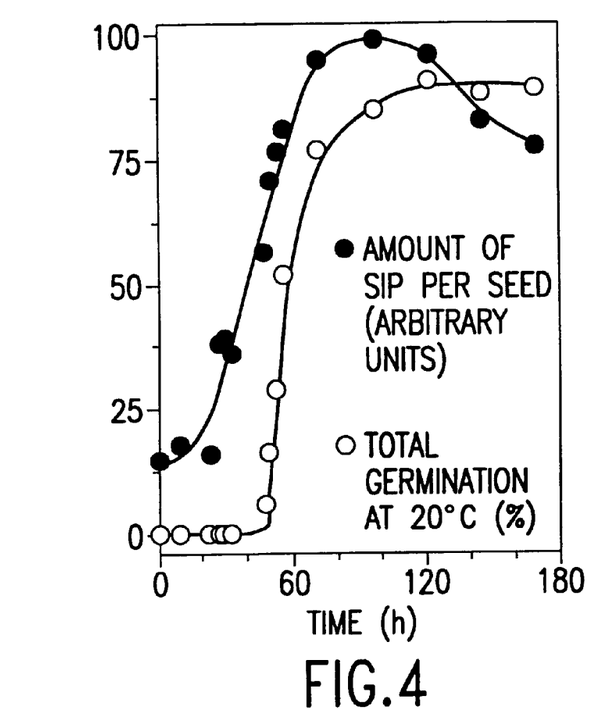
FIG. 4 is a graph showing the development of the total germination rate of the seeds as a function of the incubation time and of the induction of the SIP protein.

FIG. 4 shows the development of the total germination rate of the seeds (O) as a function of the incubation time and of the induction of the SIP protein ('), the latter being detected specifically by carrying out ELISA tests with anti-SIP antibodies. The results concerning the SIP protein are expressed in arbitrary units (100% corresponding to the maximum level obtained after 96 hours of germination) and per seed. It can be seen that the SIP protein is present at a base level (10 to 15% of the maximum level) in dry seeds, and that its expression level is multiplied by a factor of 6 to 7 during germination. A large quantity of SIP is synthesized before the radicules appear. Finally, the SIP protein disappears slowly when the batch of seeds reaches its maximum germination percentage (between 90 and 130 hours).

Figure 5:
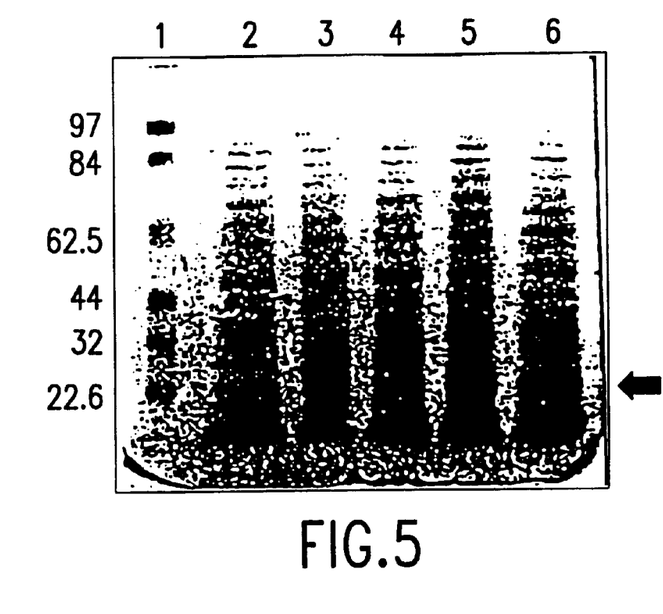
FIG. 5 is a polyacrylamide gel depicting the development of the protein profile in the proteinic extract during soaking and germination.

FIG. 5 shows the development of the protein profile in the proteinic extract during soaking and germination at 20° C. after analysis of the proteins in a 20% polyacrylamide gel containing SDS (PhastSystem by Pharmacia) and staining of the proteins with Coomassie Blue. FIG. 5, tracks 2, 3, 4, 5 and 6, show the protein profile of the control seeds and of seeds obtained after 13, 24, 36 and 48 hours' germination, respectively. Track 1 corresponds to the migration of standard proteins. Their molecular weight is shown on the left-hand side of the photograph in kDa. The black arrow on the right indicates the migration of the SIP protein. It can be seen that it is induced strongly during germination at 20° C.

EXAMPLE 3

Figure 6:
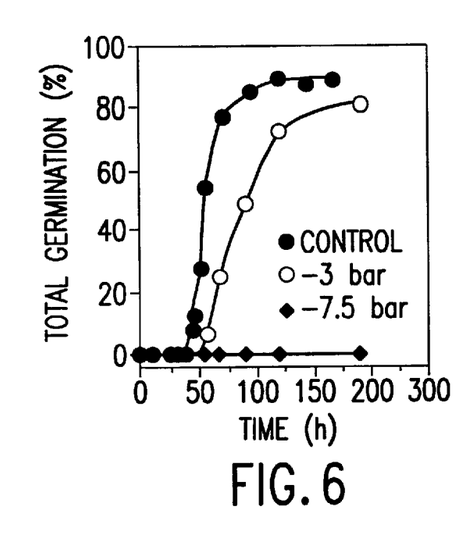
FIG. 6 is a graph showing the development of the total germination rate of seeds treated by osmoconditioning.
Figure 7:
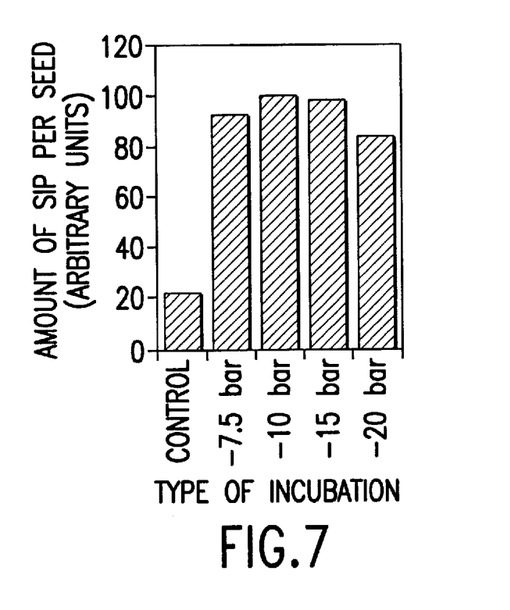
FIG. 7 is a graph showing the development of the SIP protein content of seeds treated by osmoconditioning.
Figure 8:
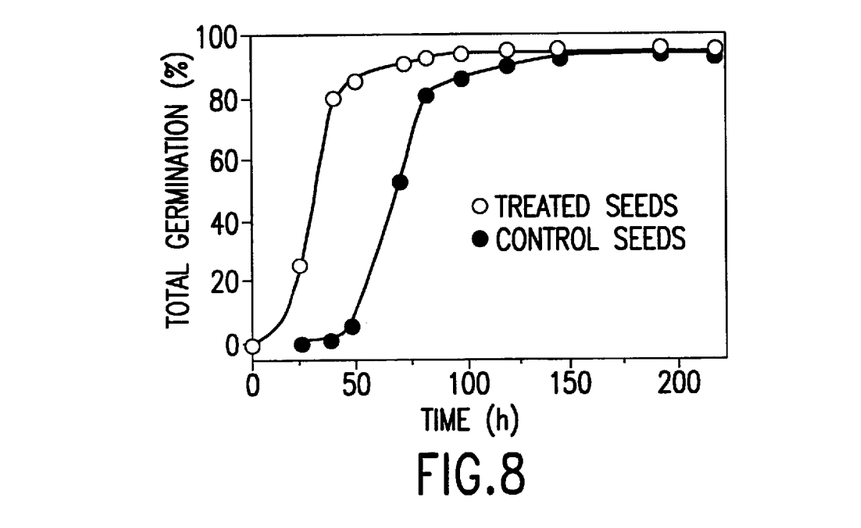
FIG. 8 is a graph showing the development of the total germination rate of seeds treated by osmoconditioning.

Osmoconditioning of Beet Seeds in the Presence of Polyethylene Glycol (PEG), and Induction of the SIP Protein The germination experiments are carried out at 20° C. and in the dark as described above. FIG. 6 shows the development of the total germination rate of the control seeds incubated in the presence of water alone ('), of seeds incubated in the presence of PEG 6000 in water, giving osmotic potentials of −3 bar (O) and −7.5 bar (♦). It shows the pronounced slowing-down of radicule emergence in samples which have been incubated in the presence of PEG 6000. This osmoconditioning treatment leads, on the one hand, to a strong induction of the SIP protein and, on the other hand, to pre-germination of the beet seeds. FIG. 7 shows the development of the SIP protein content of seeds in the course of incubation for 200 hours at 20° C. (no seed has germinated, see FIG. 6) in the presence of solutions of PEG 6000 which give osmotic potentials of −7.5 bar, −10 bar, −15 bar and −20 bar. The results which relate to the SIP protein are expressed in arbitrary units (100% corresponding to the maximum level) and per seed. It shows the strong induction of the SIP protein in the course of the treatment. The seeds incubated for 200 hours in the darkness at −7.5 bar and 20° C. are removed, washed rapidly to split them from PEG and then dried to return them to a hydration level similar to that of untreated control seeds (10% water). These seeds are germinated at 20° C. in the presence of water only, as described above. FIG. 8 shows the development of the total germination rate of the seeds treated in this manner (O) and of the control seeds ('). It shows that the treated seeds germinate much earlier, which confirms the efficacy of priming by osmoconditioning.

EXAMPLE 4

Figure 9:
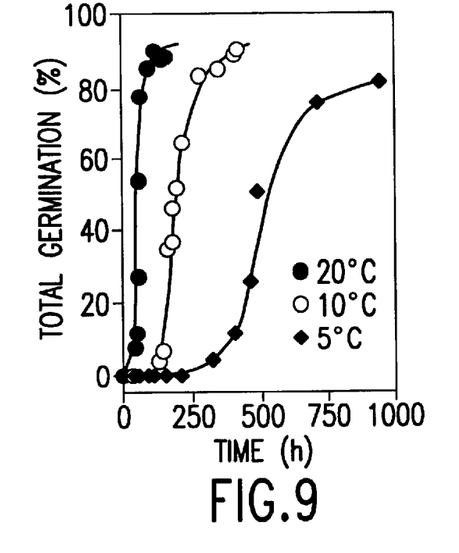
FIG. 9 is a graph showing the development of the total germination rate of seeds incubated at 20° C, 10° C and 5° C.
Figure 10:
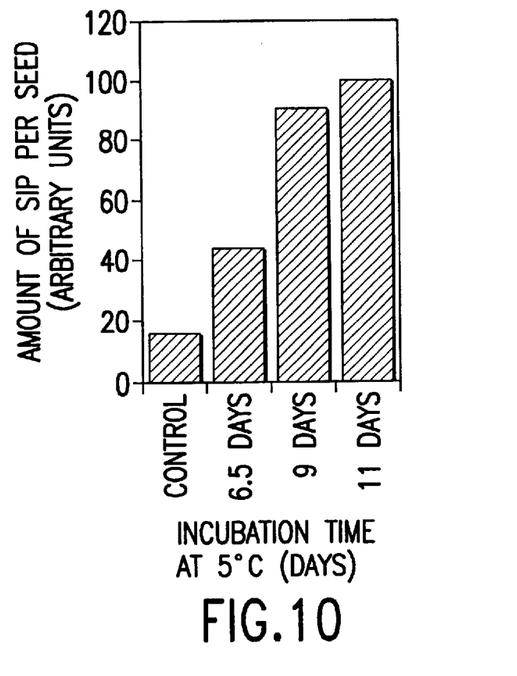
FIG. 10 is a graph showing the amount of SIP per seed at varying incubation times.
Figure 11:
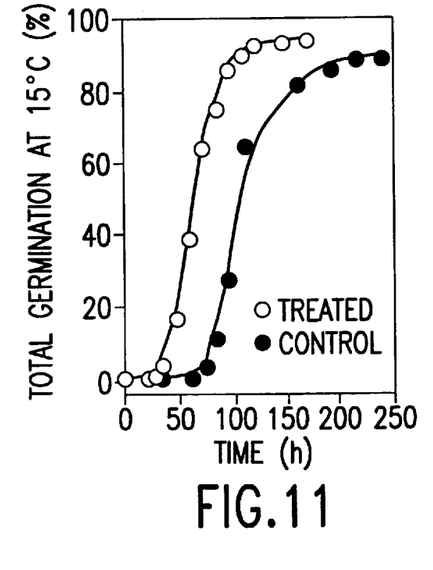
FIG. 11 is a graph showing the development of the total germination rate of seeds treated by hydroconditioning.
Figure 12:
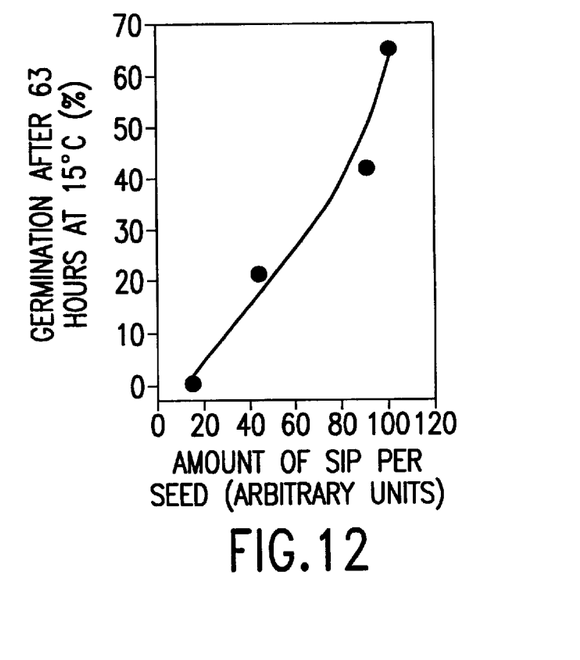
FIG. 12 is a graph showing the development of the germination rate as a function of the SIP protein level.
Figure 13:
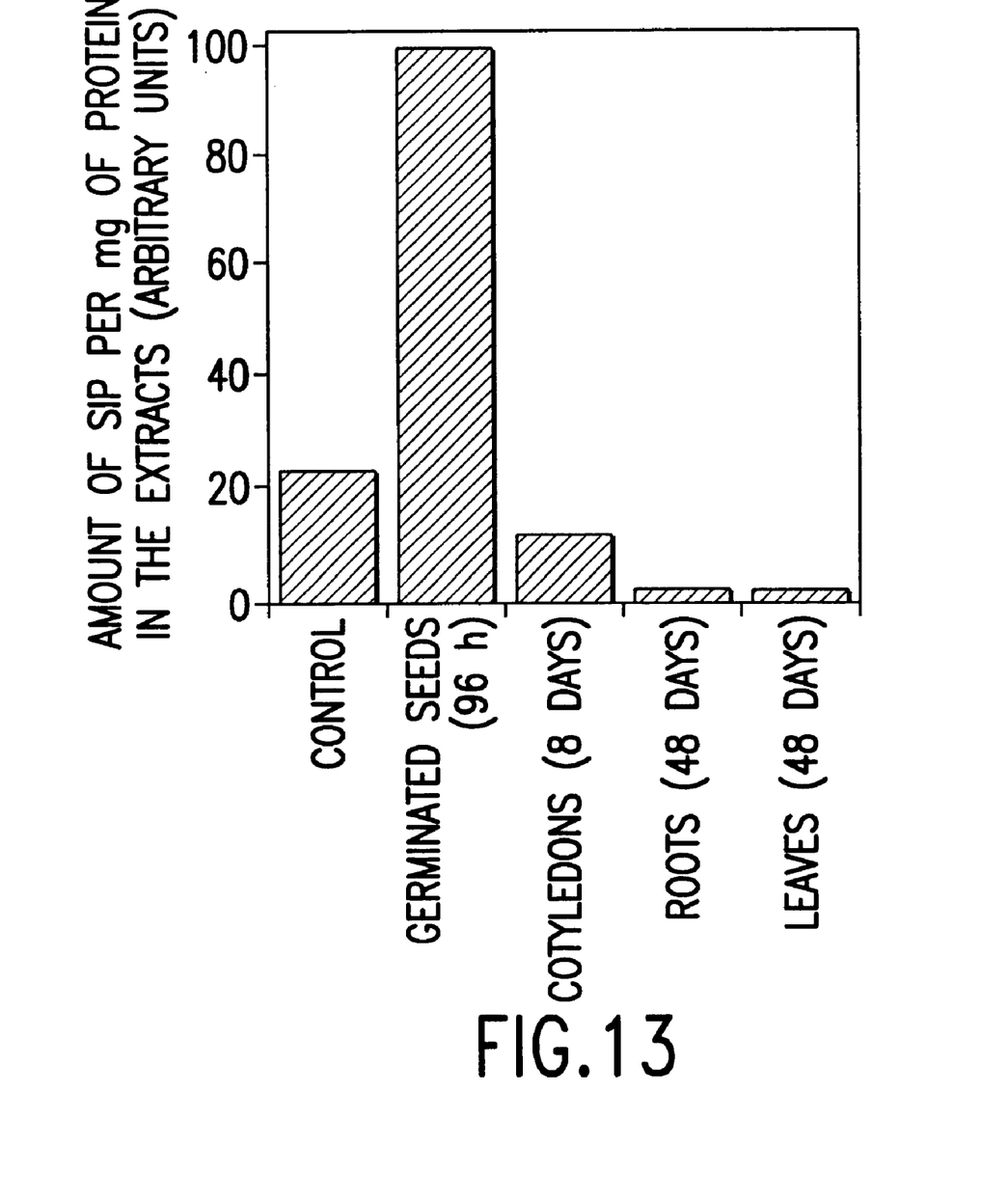
FIG. 13 is a graph showing the amount of SIP per mg. of protein in extracts from various organs.

Hydroconditioning of Beet Seeds in the Presence of Water at Different Temperatures, and Induction of the SIP Protein The experiments are carried out at different temperatures in the dark as described. FIG. 9 shows the development of the total germination rate of seeds incubated at 20° C.', 10° C. (O) and 5° C. (♦). It shows the pronounced slowing-down of radicule emergence when the temperature of the germination experiment drops. This hydroconditioning treatment leads, on the one hand, to strong induction of the SIP protein and, on the other hand, to pre-germination of the beet seeds. FIG. 9 shows the induction kinetics of the SIP protein in the course of incubation at 5° C. (no seed has germinated, see FIG. 9). The results concerning the SIP protein are expressed in arbitrary units (100% corresponding to the maximum measured after 11 treatment days) and per seed. It shows the strong induction of the SIP protein in the course of the treatment in comparison with untreated control seeds. The seeds incubated for 11 days at 5° C. in the dark are removed and then dried to return them to a hydration level similar to that of untreated control seeds (10%). These seeds are germinated at 15° C. in the presence of water alone, as described above. FIG. 11 shows the development of the total germination rate of seeds treated in this manner (O) and of control seeds ('). It shows that the treated seeds germinate much earlier, confirming the efficacy of this pre-germination method. Samples were also taken from seeds in the course of incubation at 5° C. All these samples were dried to return them to the hydration level of untreated controls (10%) and then germinated in the presence of water alone (6 ml per hundred seeds) at 15° C. FIG. 12 shows the development of the germination rate (expressed in % of seeds tested) measured after 63 hours of incubation at 15° C. as a function of the SIP protein level contained in the different samples taken during the first incubation at 5° C. It shows that a positive correlation exists between the intensity of priming and the SIP content.

EXAMPLE 5
Germination of Sugar Beet Seeds which have been Pregerminated Using the Prehydration Treatment The germination experiments are carried out at 15° C. under the conditions described in the first patent. Washed and pre-germinated seeds (J), unwashed but pre-germinated seeds (G) and untreated control seeds (E).

Figure 19:
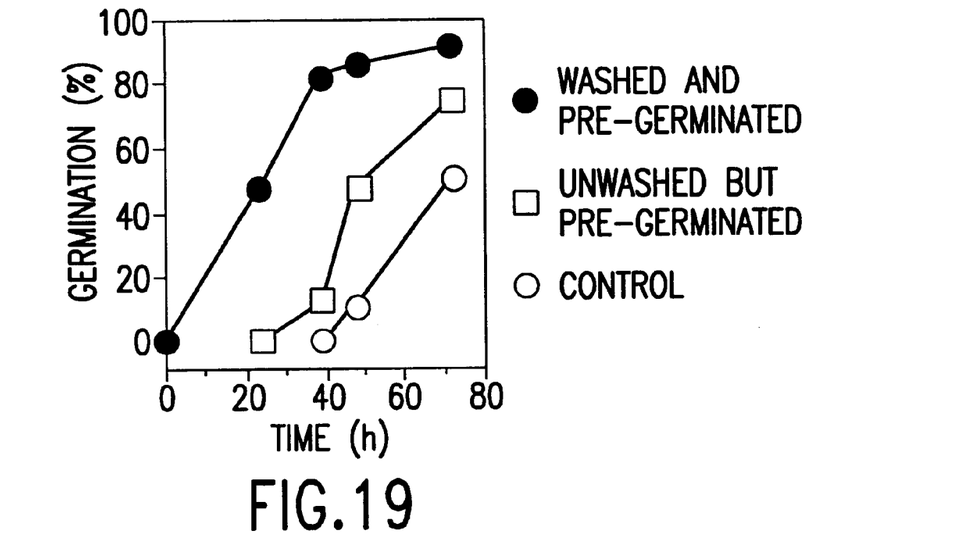
FIG. 19 is a graph depicting the germination of sugar beet seeds that have been pre-germinated.

The results are shown in FIG. 19.

EXAMPLE 6
Quantitative Determination of the Soluble and Total SIP Protein Levels (Subunit β of the 11S globulin) in Sugar Beet Seeds which have been Pre-germinated Using the Prehydration Treatment Soluble and total proteins were extracted as described in a Hepes buffer of pH 8.0, with or without SDS (2% vol/vol), respectively. The soluble and total SIP protein levels are then determined by carrying out ELISA tests with anti-SIP antibodies as described in the first patent. Columns 1 and 4, i.e. soluble and total SIP of the proteinic extracts of untreated control seeds.

Columns 2 and 5, soluble and total SIP, respectively, of the proteinic extracts of unwashed but pre-germinated seeds. Columns 3 and 6, soluble and total SIP, respectively, of the proteinic extracts of washed and pre-germinated seeds.

Figure 20:
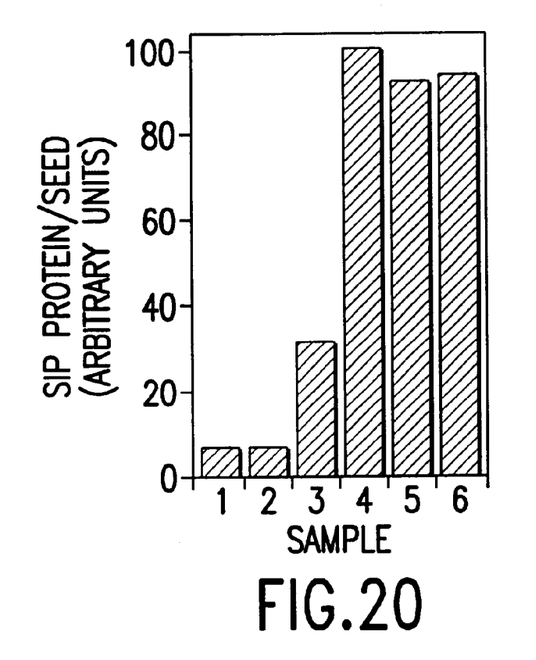
FIG. 20 is a graph depicting the amounts of soluble and total SIP in sugar beet seeds.

The results are shown in FIG. 20.

EXAMPLE 7
Distribution of the SIP Protein in the Tissue in the Course of the Growth Cycle of Beet Plants Mature beet seeds (cultivar Univers) are germinated (T=20° C.) at time zero, either on filter paper in Petri dishes (one hundred seeds and 6 ml of water per dish) or on compost to obtain plants. In the latter case, they are watered each day with water. Crude extracts of total and soluble proteins are prepared from various organs (dry seeds, seeds germinated after 96 hours, cotyledons after 8 hours, germination, roots and leaves after 48 days' germination). The results concerning the SIP protein are expressed in arbitrary units (100% corresponding to the maximum measured in the seeds which have germinated after 96 hours) and per mg of total proteins in each extract.

Figure 14:
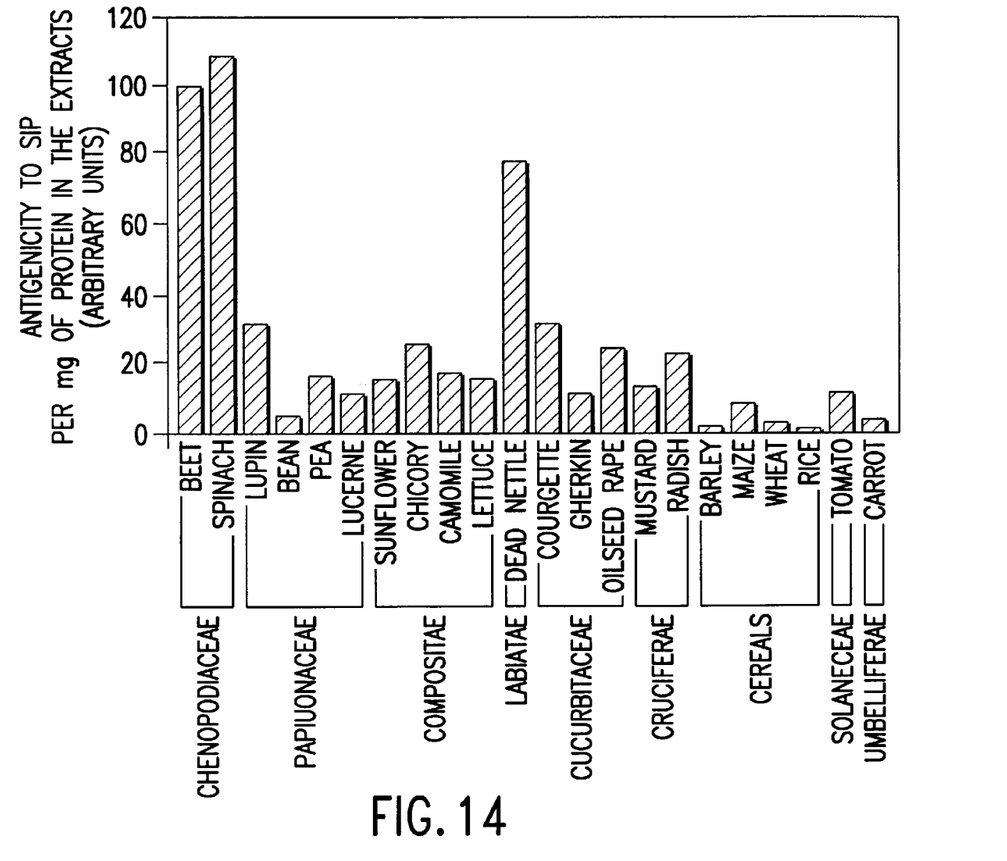
FIG. 14 is a graph depicting antigenicity to SIP in seeds of various species.
Figure 15:
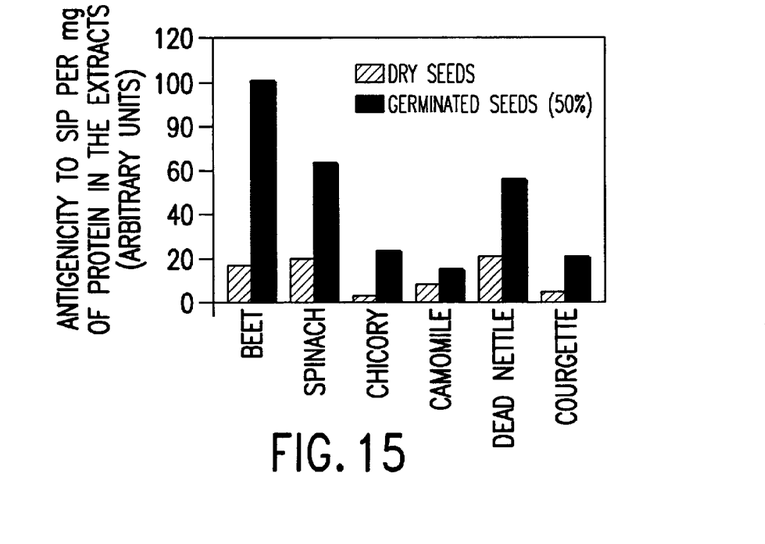
FIG. 15 is a graph depicting antigenicity to SIP in dry and germinated seeds of various species.

EXAMPLE 8
Presence of Proteins Equivalent to the SIP Protein in Other Kinds of Seeds Different batches of seeds belonging to the Chenopodiaceae (beet, spinach), Papilionaceae (lupin, bean, pea, lucerne), Compositae (sunflower, chicory, camomile, lettuce), Labiatae (dead nettle), Cucurbitaceae (courgette, gherkin), Cruciferae (oilseed rape, mustard, radish), cereals (barley, maize, wheat, rice), Solanaceae (tomato) and Umbelliferae (carrot) are germinated at 20° C. in Petri dishes as described for beet. When each batch reaches a germination percentage of 50%, the seeds are removed, and crude proteinic extracts are prepared as described for beet. These extracts are analysed using an ELISA technique for quantitatively determining their reactivity towards anti-SIP antibodies of beet. The results concerning the SIP protein are expressed in arbitrary units (100% corresponding to the level measured in beet) and per mg of total proteins in each extract. FIG. 14 shows the existence of proteins which recognize the anti-SIP antibodies in a large number of species, with the exception of cereals. FIG. 15 shows that the level of proteins equivalent to SIP in spinach, chicory, dead nettle and courgette increases greatly during the early germination phases.

EXAMPLE 9
Comparison of the Molecular Weight of the SIP Protein in Sugar Beet and Other Kinds of Seeds Different batches of seeds (sugar beet, spinach, chicory, camomile, lupin, dead nettle) are germinated at 20° C. in Petri dishes as described for beet. When each batch reaches a germination percentage of 50%, the seeds are removed, and crude proteinic extracts are prepared as described for beet. These extracts are analysed by 20% polyacrylamide gel electrophoresis in the presence of SDS (PhastSystem by Pharmacia) and by staining with Coomassie Blue or detection with anti-SIP antibodies after electrotransfer of the proteins from the gel to a nitrocellulose sheet by the method of Towbin et al. (1979).

Figure 16:
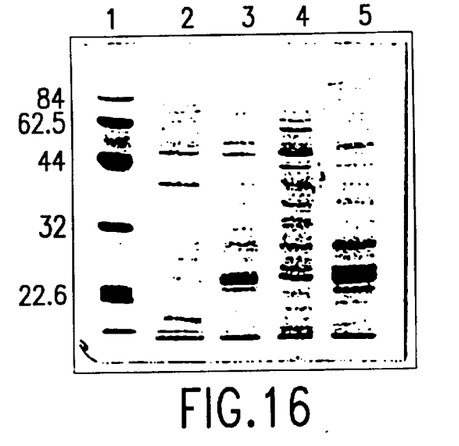
FIG. 16 is a polyacrylamide gel showing the profile of protein extracts of control and germinated beet and spinach seeds.

(A) FIG. 16 shows the analysis of beet and spinach seeds after staining with Coomassie Blue. Track 2 corresponds to control beet seeds. Track 3 corresponds to germinated beet seeds. Track 4 corresponds to control spinach seeds. Track 5 corresponds to geminated spinach seeds. It can be seen that, as in the case of beet, germinated spinach seeds contain a major soluble protein of approximately 22 kDa. The molecular weight of standard proteins is shown in kDa (track 1).

Figure 17:
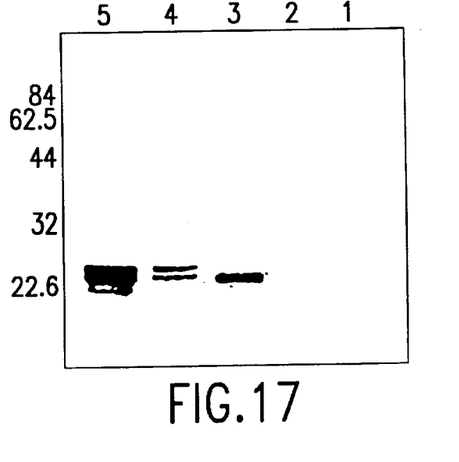
FIG. 17 depicts the samples of FIG. 16 following electrophoretic transfer onto nitrocellulose sheets and reaction with anti-SIP antibodies.

(B) FIG. 17 shows the same samples as in FIG. 16 after electrophoretic transfer of the proteins onto nitrocellulose sheets and reaction with anti-SIP antibodies. The numbering of the tracks is the same as in FIG. 16. The detection is carried out with secondary antibodies to rabbit antibodies, coupled with peroxidase (Sigma), and development of the peroxidase reaction.

Figure 18:
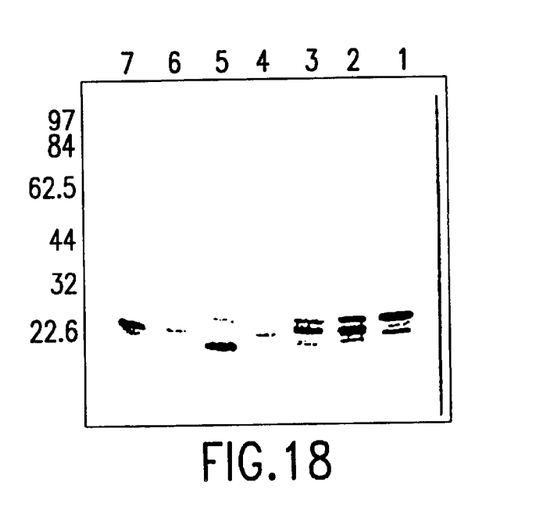
FIG. 18 shows analysis of germinated seeds of various species after electrophoresis, transfer of proteins to nitrocellulose sheets, and reaction with anti-SIP antibodies.

(C) FIG. 18 shows the analysis of germinated seeds of chicory (track 1), courgette (track 2), spinach (track 3), lupin (track 4), dead nettle (track 5) camomile (track 6) and beet (track 7) after electrophoresis, transfer of the proteins onto nitrocellulose sheets and reaction with anti-SIP antibodies. Detection is carried out with secondary antibodies to rabbit antibodies, coupled with peroxidase (Sigma), and development of the peroxidase reaction. The molecular weight of the standard proteins is given in kDa. In the case of chicory, courgette and spinach, the anti-SIP antibodies detect a small group of proteins (doublet or triplet) of a molecular weight which is very close to that of the SIP protein of beet. The synthesis of these proteins is strongly induced in the course of germination.

All these results suggest a role of the SIP protein in the controlled uptake of water of seeds in the course of germination and in the course of priming treatments (osmoconditioning, hydroconditioning and prehydration). It must be noted that the SIP protein represents the major soluble protein of soaked beet and spinach seeds. It might thus be involved in the distribution of water molecules (and/or solutes) within various parts which constitute the seed.

Within the scope of this hypothesis it is interesting to compare the properties of the SIP protein with those of plant proteins recently described by the team of Chrispeels in the United States [see, for example, Chrispeels & Maurel (1994) for a review]. In plants (bean, *Arabidopsis thaliana*), these researchers have in fact revealed the existence of membrane proteins linked to the tonoplast, which they have called aquaporins or TIP proteins ('Tonoplast Intrinsic Proteins'). This is a multigene family, and some of these proteins are expressed specifically in seeds. They are found in particular in the membrane system which encloses the vacuoles where the seed storage proteins are stored, and their role would be the maintenance of the integrity of the tonoplast in the course of dehydration of the seeds at the end of maturation, and in the course of their hydration during germination (Johnson et al., 1991). These aquaporins have molecular weights in the order of 27 kDa, which is very similar to the weight of the SIP protein. However, certain elements indicate that the two types of proteins differ considerably. a) The SIP protein can be extracted readily with an aqueous solvent, while the TIP proteins are extremely hydrophobic and can only be extracted from plant tissues in the presence of detergents (for example Triton). b) The TIP proteins, which are seed specific, are abundant in mature seeds and disappear rapidly in the course of germination Mäder & Chrispeels, 1984; Johnson et al., 1989). In contrast, the SIP protein exists at a base level in mature seeds and is induced in a substantial manner in the course of the early phases of germination.

REFERENCES

Battle, J. P. and Whittington, W. J. (1969) The relation between inhibiting substances and variability in time to germination of sugar beet clusters. *Journal of Agricultural Science* 73, 337–346.

Bewley, J. D. & Black M. (1983) in Physiology and Biochemistry of Seeds in Relation to Germination, Vol. 1, pp. 177–244, Springer-Verlag, Berlin.

Bewley, J. D. and Black, M. (1994) *Seeds. Physiology of development and germintion.* 2nd Ed. Plenum Press, New York.

Chrispeels, N. J. & Maurel, C. (1994) Plant Physiol. 105, 9–13.

Coolbear, P., Newell, A. J. & Bryant, J. A. (1987) Ann. Appl. Biol. 110, 185–194.

Dearman, J., Brocklehurst, P. A. and Drew, R. L. K. (1986) Effect of osmotic priming and ageing on onic seed germination. *Annals of Applied Biology* 108, 639–648.

Edman P. 1956. On the mechanism of the phenylisothiocyanate degradation of peptides. *Acta Chem. Scand.* 10, 761.

Edman P. 1956. A protein sequanator. *Eur. J. Biochem.* 1, 80–81.

Fincher, G. B. (1989) Annu. Rev. Plant Physiol. Plant Mol. Biol. 40, 305–346.

Hegarty, T. W. (1978) The physiology of seed hydration and dehydration, and the relation between water stress and the control of germination: a review. *Plant, Cell and Environment* 1, 101–119.

Johnson, K. D., Herman, E. M. & Chrispeels, M. J. (1989) Plant Physiol. 91, 1006–1013.

Karssen, C. M., Haigh, A., van der Toorn, P. & Weges, R. (1989) in Recent Advances in the Development and Germination of Seeds (Taylorson, R. B., ed.) NATO ASI series, Series A, Life sciences, Vol. 187, pp. 269–280.

Khan, A. A., Peck, N. H., Taylor, A. G. and Saminy, C. (1983) Osmoconditioning of beet seeds to improve emergence and yield in cold soil. *Agronomical Journal* 75, 788–794.

Lawrence, D. M., Halmer, P. and Bowles, D. J. (1990) Mobilisation of storage reserves during germinatic and early seedling growth of sugar beet. *Physiologia Plantarum* 78, 421–429.

Mäder, M. & Chrispeels, M. J. (1984) Planta 160, 330–340.

Michel, B. E. & Kaufmann, M. R. (1973) Plant Physiol. 51, 914–916.

Morris, P. C., Grierson, D. and Whittington, W. J. (1984) Endogeneous inhibitors and germination of *Bervulgaris*. *Journal of Experimental Botany* 35, 994–1002.

Müntz, K. (1996) Proteases and proteolytic cleavage of storage proteins in developing and germination dicot seeds. *Journal of Experimental Biology* 47, 605–622.

Shewry, P. R., Napier, J. A. and Tatham, A. S. (1995) Seed storage proteins: structures and biosynthesis. *The Plant Cell* 7, 945–956.

Snyder, F. W., Sebeson, J. M. and Fairley, J. L. (1965) Relation of water soluble substances in fruits of sugar beet to speed of germination of sugar beet seed. *Journal of the American Society of Sugar Beet Technologists* 13, 379–388.

Tarquis, A. M. and Bradford, K. J. (1992) Prehydration and priming treatments that advance germinatic also increase the rate of deterioration of lettuce seeds. *Journal of Experimental Botany* 43, 307–317.

Teissère, M., Sergi, I., Job C. & Job, D. (1990) Eur. J. Biochem. 193, 913–919.

Towbin, H., Staehelin, T. & Gordon, J. (1979) Proc. Natl. Acad. Sci. USA 76, 4350–4354.

The invention furthermore relates to molecular, proteinic or nucleic probes which are characterized in that they are derived from the protein (amino acid sequence of the protein, base sequence of the complementary DNA which encodes the protein) hereinabove.

The present invention furthermore relates to a method for obtaining transformed plants, characterized in that one or more copies of the gene which encodes the SIP protein according to the invention are inserted into the genome of plants which would not naturally express the SIP protein (or an equivalent protein), or which would express this protein only at a low level, so as to express, or superexpress, this protein in the seeds of the transformed plants at the moment of germination and to improve the germination capacity of these seeds.

What is claimed is:

1. A method for determining the germination capacity of seeds comprising determining the mobilization of globulin 11 S by detecting the amount of a soluble subunit thereof in extracts of said seeds, wherein the mobilization of globulin 11S is indicative of the germination capacity of said seeds.

2. A method of monitoring the stage of a seed soaking process comprising determining the mobilization of globulin 11S by detecting the amount of a soluble subunit thereof in extracts of seeds undergoing a seed soaking process, wherein the mobilization of globulin 11S is indicative of the stage of the seed soaking process.

3. The method of claim 1 or 2 wherein said seeds are from a species of Chenopodiaceae, Compositae, Labiatae or Cucurbitraceae.

4. The method of claim 1 or 2 wherein said seeds are from beet, spinach, fat hen, chicory, camomile, dead nettle or courgette.

5. The method of claim 1 or 2 wherein said soluble subunit is quantitated using an antibody.

6. The method of claim 5 wherein said antibody is an antibody against a subunit of globulin 11S of a species of Chenopodiaceae, Compositae, Labiatae or Cucurbitaceae.

7. The method of claim 6 wherein said antibody is an antibody against a subunit of globulin 11S of beet, spinach, fat hen, chicory, camomile, dead nettle or courgette.

8. The method of claim 5 wherein said antibody is an antibody against a subunit of globulin 11S of sugar beet.

9. The method of claim 5 wherein said soluble subunit is quantitated by ELISA.

10. The method of claim 2 wherein said seed soaking process is a germination or pre-germination method.

11. The method of claim 10 wherein said pre-germination method is hydroconditioning, osmoconditioning or prehydration.

* * * * *